United States Patent [19]

Ruiz

[11] Patent Number: 4,973,306
[45] Date of Patent: * Nov. 27, 1990

[54] METHOD OF PERFORMING RIGHT CORONARY ARTERY ANGIOGRAPHY

[75] Inventor: Oscar F. Ruiz, Coconut Grove, Fla.

[73] Assignee: Sherwood Medical Company, St. Louis, Mo.

[*] Notice: The portion of the term of this patent subsequent to Nov. 28, 2006 has been disclaimed.

[21] Appl. No.: 405,601

[22] Filed: Sep. 11, 1989

Related U.S. Application Data

[63] Continuation of Ser. No. 141,208, Jan. 6, 1988, Pat. No. 4,883,058.

[51] Int. Cl.⁵ .......................................... A61M 25/01
[52] U.S. Cl. ..................................... 604/53; 128/654; 128/658; 604/281
[58] Field of Search ................ 128/654, 656–658; 604/52, 53, 281

[56] References Cited

U.S. PATENT DOCUMENTS

| | | |
|---|---|---|
| 3,419,010 | 12/1968 | Williamson . |
| 3,726,269 | 4/1973 | Webster, Jr. . |
| 3,935,857 | 2/1976 | Co . |
| 3,938,501 | 2/1976 | Erickkson . |
| 4,033,331 | 7/1977 | Guss et al. . |
| 4,117,836 | 10/1978 | Erikson . |
| 4,169,464 | 10/1979 | Obrez ............................ 128/657 |
| 4,279,252 | 7/1981 | Martin . |
| 4,292,976 | 10/1981 | Banka ............................ 128/656 |
| 4,385,635 | 5/1983 | Ruiz ............................... 128/658 |
| 4,563,181 | 1/1986 | Wijayarathna et al. ....... 604/280 |
| 4,568,338 | 2/1986 | Todd .............................. 604/281 |
| 4,883,058 | 11/1989 | Ruiz ............................... 128/654 |

Primary Examiner—Ruth S. Smith
Attorney, Agent, or Firm—Andrew J. Beck; Montgomery W. Smith; Richard D. Allison

[57] ABSTRACT

An angiographic catheter includes a relatively soft, tip portion having a preformed curvature, and a resilient body portion extending therefrom having a preformed curvature in the opposite direction. A lumen extends through the catheter for the injection of angiographic dye therethrough to the right coronary artery. The part of the body portion of the catheter which it in the aortic arch of the patient during use has an amount of curvature which is less than the amount of curvature of the aortic arch, so that the body portion of the catheter is resiliently deformed where it passes through the aortic arch. The deformation results in the biasing of the tip portion of the catheter into the ostium of the right coronary artery. Upon insertion into the aorta the preformed catheter is oriented so that the curvature of the body portion of the catheter corresponds in direction to the curvature of the aortic arch, the tip portion of the catheter being disposed above the ostium of the right coronary artery with the distal end of the tip portion touching the wall of the ascending aorta. The tip portion of the catheter is moved down the wall of the ascending aorta until it reaches the ostium of the right coronary artery.

10 Claims, 2 Drawing Sheets

METHOD OF PERFORMING RIGHT CORONARY ARTERY ANGIOGRAPHY

This is a continuation of copending application Ser. No. 07/141,208 filed on Jan 6, 1988, now U.S. Pat. No. 4,883,058.

BACKGROUND OF THE INVENTION

This invention relates to catheters useful in cardiac angiography and more particularly to such catheters especially suited for the injection of a radiopaque dye into the right coronary artery.

Coronary angiography or arteriography involves the insertion of a hollow catheter into an artery at a remote point such as an arm or leg. The catheter is typically guided to the heart itself by a guide wire over which the catheter rides. The guide wire is removed before use of the catheter. Once the catheter is properly placed, a radiopaque dye is injected through the lumen of the catheter so that an x-ray machine or fluoroscope may be used to determine the physical condition of the particular part of the heart under study.

The exact placement of the tip of the catheter in the heart depends upon the type of coronary angiography to be performed. For example, in non-selective angiography the tip of the catheter is positioned in the aorta itself so that both the left and right coronary arteries can be simultaneously injected with radiopaque dye. In selective angiography, on the other hand, the tip of the catheter is actually placed in the ostium of the coronary artery which one wishes to study, in this case the right coronary artery, and the radiopaque dye is injected directly into that artery. Selective angiography produces pictures having sharp images which are extremely helpful in diagnosing and treating coronary diseases.

Heretofore, some catheters used for selective right coronary artery angiography have not always retained their positions in the ostium of the right coronary artery during the procedure. As a result the radiopaque dye was not wholly injected into the right coronary artery and the images obtained were not as satisfactory as could be desired. While some catheters fall or pop out of the ostium, others are difficult to insert properly into the ostium initially. In addition, some prior catheters have been known to dive too far into the right coronary artery itself, which can cause a spasm of the artery.

It is also important that the catheter be made of the proper materials. Although a certain hardness and rigidity is desired to allow maintain the catheter in position in the ostium once the tip is inserted therein, a catheter which is too rigid is difficult to position properly. Moreover, a relatively hard tip on the catheter can result in the dislodging of plaque from the vessel walls, which is not desirable.

Several catheters have been proposed or developed to solve some of the above difficulties. For example, U.S. Pat. No. 3,935,857 to Co discloses a cardiac catheter which is alleged to be useful in both right coronary and left coronary selective arteriography. On the other hand, Dr. Melvin P. Judkins in Chapter 7 of *Coronary Arteriography and Angioplasty* "1985" (McGraw-Hill) discloses differently shaped catheters for right coronary and left coronary selective arteriography.

The Judkins right coronary catheter has a preformed curvature which is designed to assist in the placement of the catheter tip in the ostium of the right coronary artery and to help hold the tip in place during the procedure. Because of the particular configuration chosen for the Judkins right coronary catheter, it is necessary for the catheter to be made in a number of different sizes to accommodate different patients. It is also necessary in using the Judkins right coronary catheter to physically rotate the catheter approximately 180 degrees once the catheter is in the heart to make it assume the proper position to enter the ostium of the right coronary artery. As Dr. Judkins points out in the aforementioned chapter, this rotation must be done very slowly and commonly gives rise to error in placement of the catheter.

SUMMARY OF THE INVENTION

Among the various objects and features of the present invention may be noted the provision of a catheter particularly suited for use in selective arteriography of the right coronary artery.

Another object of the present invention is to provide a method of using a catheter which is relatively easy to place in the ostium of the right coronary artery.

A further object of the present invention is to provide a method of using a right coronary angiographic catheter to selectively image the right coronary artery of a patient.

Other objects and features will be in part apparent and in part pointed out hereinafter.

Briefly, a right coronary artery angiographic catheter of the present invention includes a relatively soft, distal tip portion which has a preformed curvature in a first direction, and a body portion extending proximally from the tip portion. The body portion has a preformed curvature in a second direction, opposite the direction of curvature of the tip portion, and is resilient so that it tends to assume its preformed curvature when bent. A lumen extends from the distal end of the tip portion through at least a substantial part of the body portion, the lumen being suitable for the injection of angiographic dye therethrough to exit from the distal end of the tip portion of the catheter. The body portion has an amount of curvature in a second segment which is less than the amount of curvature of the aortic arch of a human being, the second segment being that part of the body portion disposed in the aortic arch when the tip portion is disposed in the ostium of the right coronary artery so that the body portion of the catheter is resiliently deformed where it passes through the aortic arch. The deformation results in the biasing of the tip portion of the catheter into the ostium of the right coronary artery when in use.

The method of using the catheter of the present invention includes the steps of inserting the preformed, hollow catheter through the aorta to a predetermined position above the ostium of the right coronary artery and orienting the preformed catheter so that the curvature of the body portion of the catheter corresponds in direction to the curvature of the aortic arch with the tip portion of the catheter disposed above the ostium of the right coronary artery and the distal end of the tip portion touching the wall of the ascending aorta. Then the tip portion of the catheter is moved down the wall of the ascending aorta in a rotatory manner using the catheter torque and applying small injections of radiopaque dye until the ostium of the right coronary artery is located and reached. There the tip portion of the catheter is biased into the ostium of the right coronary artery as a result of the tendency of the body portion of the catheter to assume its preformed curvature from which it has been deformed in passing through the aortic arch. Once the catheter is placed, an arteriographic dye is injected through the hollow catheter into the right coronary artery.

BRIEF DESCRIPTION OF THE DRAWINGS

In the drawings.

Similar reference characters indicate similar parts throughout the several views of the drawings.

DESCRIPTION OF THE PREFERRED EMBODIMENT

Figure 1:
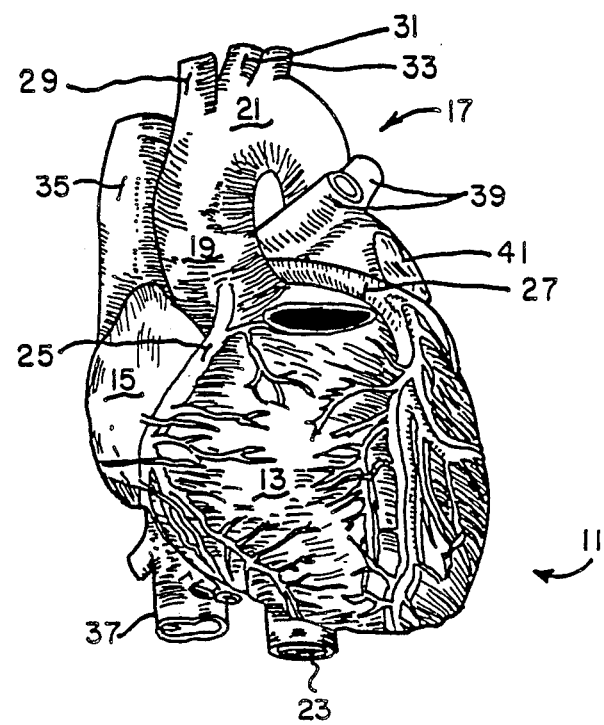
FIG. 1 is a perspective view of the human heart illustrating the relative placement of the right coronary artery, the ascending aorta, and the aortic arch.

A typical human heart 11 (FIG. 1) includes a right ventricle 13, a right auricle 15, and a left ventricle (not shown) and left auricle 41. The aorta, labelled 17, arises from the aortic opening of the left ventricle and consists of three parts: the ascending aorta 19, the aortic arch 21, and the descending aorta 23. At the base of the ascending aorta is located the ostia for the right coronary artery 25 and the left coronary artery 27. At the top of the aortic arch the brachiocephalic trunk 29, the left common carotid artery 31, and the left subclavian artery 33 branch off from the aorta.

Also shown in FIG. 1, although of no special relevance to the present invention, are the superior vena cava 35, the inferior vena cava 37, the left pulmonary veins 39, and the left auricle 41.

A catheter 43 (FIGS. 2 and 3) of the present invention is specially configured to be inserted through aorta 17 into the ostium of right coronary artery 25. More particularly, catheter 43 is inserted into a suitable artery, such as the femoral artery (not shown) and is directed by means of a conventional guide wire (not shown) to a position in the ascending aorta 19 somewhat above the ostium of right coronary artery 25 The guide wire is then withdrawn and the tip of catheter 43 is moved into the ostium as described below in detail.

Figure 2:
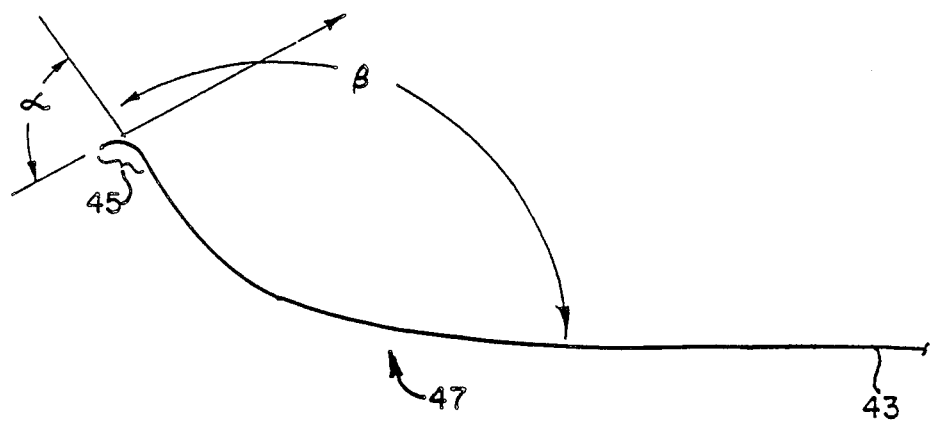
FIG. 2 is a side elevation of the catheter of the present invention illustrating the overall configuration thereof.

As can be seen from FIG. 2, catheter 43 includes a tip portion 45 having a preformed curvature formed therein in a conventional manner. This curvature is represented by the angle alpha between the two legs cf tip portion 45. This angle in FIG. 2 is 84.5 degrees, although an angle of approximately ninety degrees is also acceptable. This angle is chosen so that the tip portion 45 of catheter 43 will remain securely in the ostium of right coronary artery 25 once the catheter is placed. It is a function of the angle made between the ascending aorta 19 and the right coronary artery 25.

Figure 3:
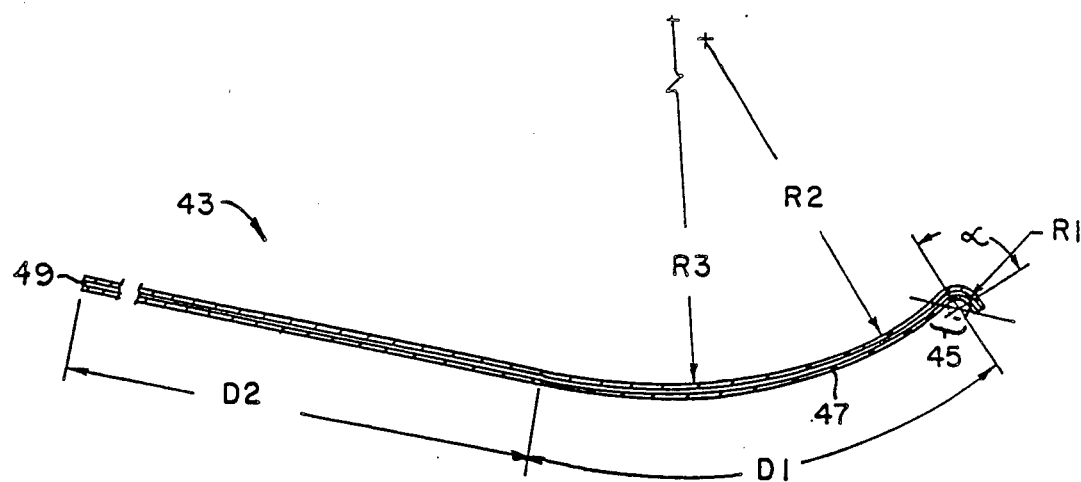
FIG. 3 is a cross-sectional view of the catheter of the present invention.

Proximal from tip portion 45 of catheter 43 is a body portion 47 extending from the tip portion to the proximal end of the catheter. Body portion 47 also has a preformed curvature formed therein by conventional means. As can be seen in FIGS. 2 and 3, the radius of curvature of the preformed curvature of body portion 47 is much larger than that of tip portion 45. Moreover, the angle beta formed by the legs of body portion 47 is also larger than the corresponding angle alpha of the tip portion. For example, the angle beta is approximately 125 degrees. The curvature of body portion 47 is chosen to correspond to the average curvature of the normal ascending aorta 19 in humans (although the present invention also works well with abnormal ascending aortas) and is in the opposite direction from the curvature of tip portion 45.

It is preferred that tip portion 45 be relatively soft in comparison to body portion 47. This is accomplished by making catheter 43 in accordance with the teachings of U.S. Pat. No. 4,385,635 to Ruiz.

As can be seen in FIG. 3, catheter 43 has a lumen 49 extending axially through the catheter and terminating at the open distal tip of the catheter. This lumen allows radiopaque dye to be injected through the catheter into the right coronary artery once the catheter is properly placed.

The angle alpha in FIG. 3 is measured at right angles to the legs of tip portion 45 and is taken with respect to a generating circle having a radius R1 which defines the curvature of tip portion 45. Radius R1 is preferably five millimeters and the maximum distance tip portion 45 can extend into the right coronary artery with this catheter configuration is approximately ten millimeters. These dimensions are chosen to ensure firm retention of the tip portion in the ostium of the right coronary artery without unduly increasing the possibility of spasm of the artery caused by "diving in", or over-insertion, of tip portion 45. The length and configuration of tip portion 45, as well as the opposite curvature of the body portion from the curvature of the tip portion permits insertion of the tip portion 45 into the ostium 25A only to the desired extent. Moreover, this configuration ensures that the distal end of tip portion 45 remains generally perpendicular to body portion 47 and that the catheter will not "roll-up" during placement.

The segment of body portion 47 immediately proximate tip portion 45 has a radius of curvature R2 of, for example, approximately 100 millimeters. This curvature smoothly changes as one moves proximally away from the tip portion to one having a radius of curvature R3 of approximately 150 millimeters. This curvature ends a distance D1 (approximately 130 millimeters) from the distal end of the catheter, and the remaining portion of the catheter over a distance D2 is generally straight. For a catheter 43 designed for femoral entry, distance D2 may be, for example, approximately ninety centimeters.

Figures 4A, 4B, 4C:
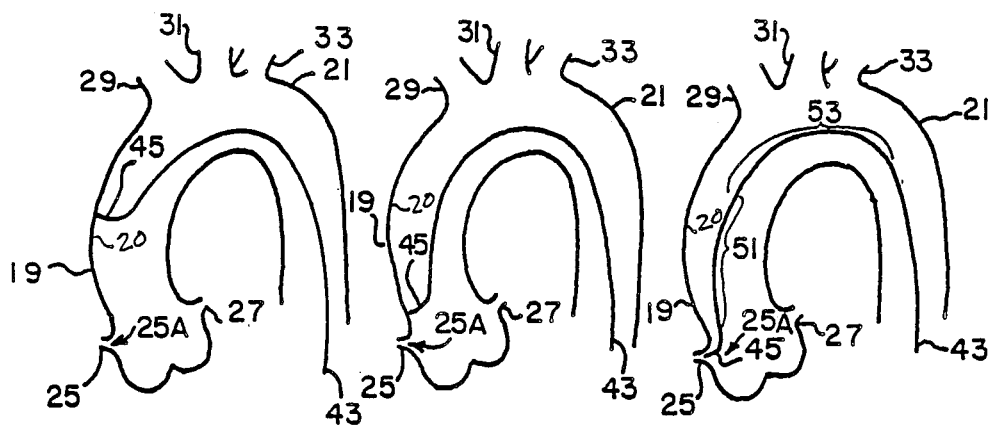
FIG. 4A-4C are semidiagrammatic views of the catheter of the present invention in the process of being placed in the ostium of the right coronary artery.

The actual placement of catheter 43 is illustrated in FIGS. 4A-4C. As shown in FIG. 4A, the tip portion 45 of catheter 43 is inserted through the aorta to a position within the ascending aorta 19 where the distal tip of the catheter is disposed above the ostium 25A of right coronary artery 25 with the end of the tip touching the inner wall of ascending aorta 19 above the ostium. This insertion is preferably performed using a guide wire that straightens the preformed curvature of tip portion 45 during insertion through the descending aorta and aortic arch into the ascending aorta. The guide wire is retracted to allow tip portion 45 to assume its preformed curvature. The tip portion 45 is then oriented so that the end of the tip portion is pointed toward and in contact with the right inner wall 20 of the ascending aorta, as shown in FIG. 4A for example. The tip portion is then moved downwardly as shown in FIGS. 4B and 4C, contacting the right inner wall 20 of the ascending aorta, by physically applying a torque to the proximal end of the catheter to cause the catheter tip to rotate somewhat, while injecting small amounts of radiopaque dye, until the rotatory motion and injections reveal that the tip portion 45 has reached the ostium 25A (FIG. 4C). At this point, tip portion 45 is biassed into the ostium by the body portion of catheter 43. More particularly, body portion 47 includes a first segment 51 and a second segment 53. As can be seen by examining FIGS. 3 and 4C, second segment 53 as shown in FIG. 4C is deformed because no part of body portion 47 has a curvature as great as that of the aortic arch in which second segment 53 is disposed. Body portion 47 is resilient, however, so the deformation caused by aortic arch 21 causes tip portion 45 to be forced to the left as shown in FIG. 4C so that it remains firmly in place in ostium 25A.

Note that with catheter 43, there is no need for the user to accurately rotate the catheter to ensure proper placement. Nor is there any significant danger of the catheter diving into the right coronary artery since the configuration of the tip portion prevents over-insertion of the catheter.

Numerous variations, within the scope of the appended claims, will be apparent to those skilled in the art in light of the foregoing description and accompanying drawings. These variations are merely illustrative.

Having thus described the invention, what is claimed and desired to be secured by Letters Patent is:

1. A method of inserting a catheter into the ostium of the right coronary artery of a human being comprising the steps of:
   inserting a catheter having a catheter body through the aortic arch into the ascending aorta of the human being such that a tip portion of the catheter is disposed above the ostium of the right coronary artery;
   orienting the catheter so that an open distal end of said catheter tip portion is pointed toward and in contact with the inner wall of said ascending aorta;
   advancing the catheter tip portion toward the ostium of the right coronary artery by moving the distal end along and contacting said inner wall while biassing the tip portion of the catheter toward the inner wall of the ascending aorta by resiliently deforming the catheter body; and
   inserting the distal open end of the tip portion in the ostium of the right coronary artery responsive to the advancing and biassing steps.

2. The method of insertion as set forth in claim 1 wherein the catheter is inserted into the ascending aorta in an initial oriented position wherein the catheter body corresponds with the direction of curvature of the aortic arch and the distal end of the catheter tip portion contacts the inner wall of the ascending aorta so that the catheter tip portion may enter the ostium of the right coronary artery without being substantially rotated from the initial oriented position.

3. The method of insertion as set forth in claim 1, wherein the method further includes the step of guiding the catheter along the aorta with a guide wire disposed in the catheter until the catheter reaches the vicinity of the top of the aortic arch and then removing the guide wire before the tip portion of the catheter is advance further towards the wall of the ascending aorta.

4. The method of insertion as set forth in claim 1, wherein the method further includes the step of injecting a dye through a lumen of the catheter.

5. The method of insertion of claim 1, further including the step of injecting a dye through a lumen in the catheter and imaging the dye to determine the position of the catheter tip in the ascending aorta.

6. The method of insertion of claim 1, further including the steps of injecting an arteriographic dye through a lumen in the catheter and selectively imaging the right coronary artery.

7. A method of inserting a catheter into the ostium of the right coronary artery of a human being comprising the steps of:
   inserting a preformed, hollow catheter through the aorta to a predetermined position above the ostium of the right coronary artery, said preformed catheter having a relatively soft, distal tip portion, said tip portion having a curvature in a first direction, said catheter further having a body portion proximal the tip portion, said body portion having a curvature in a second direction opposite the direction of the curvature of the tip portion, said body portion being resilient so that it tends to assume its preformed curvature, said inserting step further including orienting the preformed catheter so that the curvature of the body portion of the catheter corresponds in direction to the curvature of the aortic arch, the tip portion of the catheter being disposed above the ostium of the right coronary artery with the distal end of the tip portion biassed into contact with the wall of the ascending aorta;
   moving the tip portion of the catheter down the wall of the ascending aorta until it reaches the ostium of the right coronary artery, said body portion having an amount of curvature where it passes through the aortic arch which is less than the curvature of the aortic arch so that the body portion is resiliently deformed where it passes through the aortic arch due to the greater curvature of the aortic arch; and
   biassing the tip portion of the catheter into the ostium of the right coronary artery, said biassing resulting from the tendency of the body portion of the catheter to assume its preformed curvature from which it has been deformed in passing through the arch.

8. The method as set forth in claim 7 wherein the catheter is inserted into the ascending aorta in its oriented position with the curvature of the body portion corresponding in direction to the curvature of the aortic arch and the distal end of the tip portion touching the wall of the ascending aorta so that the tip portion may enter the ostium of the right coronary artery without being substantially rotated from the initial oriented position.

9. The method as set forth in claim 7 wherein the inserting step includes the step of guiding the catheter along the aorta with a guide wire disposed in the lumen of the hollow catheter until the catheter reaches the vicinity of the top of the aortic arch, and then removing the guide wire before the tip portion of the catheter moves down the wall of the ascending aorta.

10. The method as set forth in claim 7 wherein the method further includes the step of injecting a dye through a lumen in the hollow catheter.

* * * * *